United States Patent [19]

Kuhn et al.

[11] Patent Number: 5,451,694
[45] Date of Patent: Sep. 19, 1995

[54] PROCESS FOR PREPARING SUBSTITUTED 2-CYANOCINNAMIC ESTERS

[75] Inventors: Walter Kuhn, Holzminden; Werner Marks, Breörde; Thomas Thielmann; Erich Dilk, both of Holzminden, all of Germany

[73] Assignee: Haarmann & Reimer GmbH, Holzminden, Germany

[21] Appl. No.: 230,981

[22] Filed: Apr. 22, 1994

[30] Foreign Application Priority Data

Apr. 29, 1993 [DE] Germany ............... 43 14 035.1

[51] Int. Cl.$^6$ ............................................. C07C 253/30
[52] U.S. Cl. ......................................................... 558/374
[58] Field of Search ............................................ 558/374

[56] References Cited

U.S. PATENT DOCUMENTS

| | | | |
|---|---|---|---|
| 2,623,060 | 12/1952 | Cragoe | 260/465 D |
| 3,644,466 | 2/1972 | Strobel et al. | 260/465 D |
| 4,178,303 | 12/1979 | Lorenz et al. | 260/465 D |

FOREIGN PATENT DOCUMENTS

0430023 6/1991 European Pat. Off. .
1293982 10/1972 United Kingdom .

OTHER PUBLICATIONS

J. Org. Chem., vol. 15, pp. 381–390 (1950); "The Synthesis of α,α-disubstituted Succinic Acids . . ."; Cragoe, et al.

Organic Reactions, vol. 15, pp. 204, 238, 239, 265 & 414; Chapter 2, "The Knoevenagel Condensation", Jones, (No date).

*Primary Examiner*—Joseph Paul Brust
*Attorney, Agent, or Firm*—Sprung Horn Kramer & Woods

[57] ABSTRACT

In the preparation of substituted 2-cyanocinnamic esters by the Knoevenagel condensation of cyanoacetic esters and carbonyl compounds, the reaction times for obtaining high yields can be considerably reduced by using $C_3$–$C_6$-monocarboxylic acids and ammonium compounds as catalysts.

3 Claims, No Drawings

PROCESS FOR PREPARING SUBSTITUTED 2-CYANOCINNAMIC ESTERS

The invention relates to an improved process for preparing substituted 2-cyanocinnamic esters by the Knoevenagel condensation of a cyanoacetic ester and a carbonyl compound.

Substituted 2-cyanocinnamic esters are excellent UV absorbers; of. U.S. Pat. No. 3,644,466. They are generally prepared by the Knoevenagel condensation; see EP-A 430 023; U.S. Pat. No. 2,623,060 and 4,178,303; JP-A 1,293,982. The catalyst used is preferably a mixture of glacial acetic acid and ammoniumacetate, the reaction water formed being removed as an azeotrope with an organic solvent such as cyclohexane, hexane, heptane, benzene, toluene or xylene.

For the achievement of high yields, the processes of the prior art require long reaction times, and these long reaction times at higher temperatures also favour the formation of unwanted by-products.

The object of the invention was therefore to provide an economical process for preparing substituted 2-cyanocinnamic esters. It has surprisingly been found that this object can be achieved by the use of a $C_3$–$C_6$-monocarboxylic acid in the presence of ammonium ions. The process of the invention considerably reduces the reaction times for obtaining good yields, and the ammonium compound can be added all at once without concern about the formation of unwanted by-products.

The invention accordingly provides a process for preparing compounds of the formula

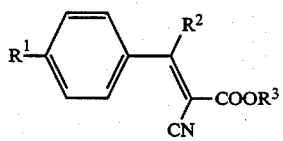

(I)

in which
$R^1$ = H, $C_{1-4}$-alkyl or $C_{1-4}$-alkoxy,
$R^2$ = H, $C_{1-4}$-alkyl or phenyl and
$R^3$ = $C_{1-12}$-alkyl,
by reaction of a cyanoacetic ester of the formula

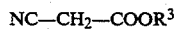

(II)

with a carbonyl compound of the formula

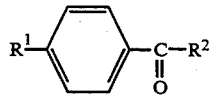

(III)

in the absence of organic solvents and in the presence of a $C_3$–$C_6$-monocarboxylic acid and an ammonium compound.

Preferred cyanoacetic esters II include, for example, ethyl cyanoacetate, isoamyl cyanoacetate and isooctyl cyanoacetate.

Preferred carbonyl compounds III include, for example, benzaldehyde, anisaldehyde and benzophenone.

The molar ratio of III/II can vary within wide ranges and is generally from 0.1 to 10, preferably from 0.5 to 2.

Preferred $C_3$–$C_6$-monocarboxylic acids are, for example, n-butyric acid, n-valeric acid and n-caproic acid, but in particular propionic acid. The amount of monocarboxylic acid can vary widely and is generally from 0.1 to 10 mol, preferably from 0.5 to 2 mol, per tool of cyanoacetic ester II.

Suitable ammonium compounds include ammonia and ammonium salts, preferably ammonium salts of $C_2$–$C_6$-monocarboxylic acids such as, for example, ammonium acetate. The amount of ammonium compound is not very critical and is usually from 0.01 to 0.6 mol, preferably from 0.05 to 0.2 mol, per mol of cyanoacetic ester II.

The reaction temperature my be from 70° to 130° C., preferably from 100° to 110° C. The monocarboxylic acid/water mixture can be distilled off at atmospheric pressure or at reduced pressure, for example at from 20 to 400 mbar. As soon as no more water separates out, the reaction can be taken as having ended. This is generally the case after from 3 to 6 hours. The reaction product is washed in a usual manner and distilled for further purification.

The percentages given in the examples below are in each case percentages by weight.

EXAMPLES

Example 1

Preparation of isooctyl 2-cyano-3,3-diphenylacrylate a) 285 g of isooctyl cyanoacetate, 400 g of benzophenone, 200 g of propionic acid and 20 g of ammonium acetate are mixed and heated to 100° C. A propionic acid/water mixture is distilled off over a period of 5 h at a pressure of from 200 to 20 mbar. The crude reaction mixture is washed twice with 250 g portions of water and subsequently distilled. 172 g of a first fraction, comprising 148 g of benzophenone and 18 g of isooctyl cyanoacetate, and 467 g of product are obtained.

The yield, based on converted cyanoacetic ester, is 94%.

b) 280 g of isooctyl cyanoacetate, 244 g of benzophenone, 200 g of propionic acid and 50 g of ammonium acetate are mixed and heated to 100° C. A propionic acid/water mixture is distilled off over a period of 6 h at a pressure of from 200 to 40 mbar. The crude reaction mixture is washed twice with 300 g portions of water and subsequently distilled. 98 g of a first fraction, containing unreacted benzophenone and isooctyl cyanoacetate, and 381 g of product are obtained.

The yield, based on the amount of benzophenone used, is 79%.

c) 320 g of isooctyl cyanoacetate, 244 g of benzophenone, 200 g of propionic acid and 50 g of ammonium acetate are mixed and heated to 100° C. A propionic acid/water mixture is distilled off over a period of 5 h at a pressure of from 250 to 40 mbar. The crude reaction mixture is washed twice with 300 g portions of water and subsequently distilled. 124 g of a first fraction, containing unreacted benzophenone and isooctyl cyanoacetate, and 390 g of product are obtained.

The yield, based on the amount of benzophenone used, is 80%.

For comparison:
1. Preparation of isooctyl 2-cyano-3,3-diphenylacrylate according to EP-A 430 023 with cyclohexane as azeotrope former at 88° C./22 h and repeated addition of catalyst. The yield, based on the amount of benzophenone used, is 73%.

Preparation of isooctyl 2-cyano-3,3-diphenylacrylate with toluene as azeotrope former at 118° C. 709 g of isooctyl cyanoacetate, 546 g of benzophenone, 363 g of acetic acid, 139 g of ammonium acetate and 520 g of toluene are mixed. Water is removed at a liquid-phase temperature of 118° C. over a period of 8 h. After washing with water and distillation, 735 g of product are obtained. The yield, based on the amount of benzophenone used, is 65%.

Example 2

Preparation of isooctyl 2-cyano-3-(4-methoxyphenyl)acrylate a) 285 g of isooctyl cyanoacetate, 300 g of p-anisaldehyde, 200 g of propionic acid and 20 g of ammonium acetate are mixed and heated to 100° C. A propionic acid/water mixture is distilled off over a period of 3 h at a pressure of from 390 to 30 mbar. The crude reaction mixture is washed twice with 250 g portions of water and subsequently distilled. 58 g of p-anisaldehyde first fraction and 399 g of product are obtained.

The yield, based on cyanoacetic ester used, is 86%.

b) 143 g of isooctyl cyanoacetate, 99 g of p-anisaldehyde, 100 g of propionic acid and 10 g of ammonium acetate are mixed and heated to 100° C. A propionic acid/water mixture is distilled off over a period of 3 h at a pressure of from 390 to 30 mbar. The crude reaction mixture is washed twice with 125 g portions of water and subsequently distilled. 215 g of product are obtained.

The yield, based on p-anisaldehyde used, is 95%.

We claim:

1. A process for preparing compounds of the formula

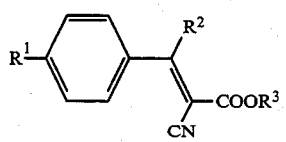

in which
$R^1$=H, $C_{1-4}$-alkyl or $C_{1-4}$-alkoxy,
$R^2$=H, $C_{1-4}$-alkyl or phenyl and
$R^3$=$C_{1-12}$-alkyl,
by reacting of a cyanoacetic easter of the formula

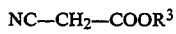

with a carbonyl compound of the formula

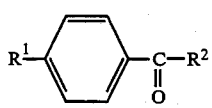

at a temperature range of 70° to 130° C. in the presence of a $C_3$–$C_6$-monocarboxylic acid selected from the group consisting of propionic acid, butyric acid, n-valeric acid and n-caproic acid; and an ammonium compound selected from the group consisting of ammonia and ammonia salts of $C_2$–$C_6$ monocarboxylic acids;

wherein there are no additional organic solvents other than the monocarboxylic acid and the ammonium compound.

2. The process according to claim 1, wherein the $C_3$–$C_6$-monocarboxylic acid is propionic acid.

3. The process according to claim 1, wherein the ammonium compound is ammonium acetate.

* * * * *